(12) United States Patent
Tornay et al.

(10) Patent No.: US 9,349,545 B2
(45) Date of Patent: *May 24, 2016

(54) METHOD FOR PRODUCING MICROCARRIERS

(71) Applicant: MYCARTIS NV, Zwijnaarde/Ghent (BE)

(72) Inventors: Raphael Tornay, Illarsaz (CH); Nicolas Demierre, Chatel-St-Denis (CH); Stephan Gamper, Lausanne (CH); Philippe Renaud, Lausanne (CH)

(73) Assignee: MYCARTIS NV, Zwijnaarde/Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/414,174

(22) PCT Filed: Jul. 22, 2013

(86) PCT No.: PCT/EP2013/065442
§ 371 (c)(1),
(2) Date: Jan. 12, 2015

(87) PCT Pub. No.: WO2014/016262
PCT Pub. Date: Jan. 30, 2014

(65) Prior Publication Data
US 2015/0162141 A1     Jun. 11, 2015

(30) Foreign Application Priority Data

Jul. 24, 2012   (EP) ..................................... 12177718

(51) Int. Cl.
*H01G 13/06*    (2006.01)
*B01L 3/00*    (2006.01)
(Continued)

(52) U.S. Cl.
CPC ................ *H01G 13/06* (2013.01); *B01L 3/508* (2013.01); *B01L 3/502707* (2013.01);
(Continued)

(58) Field of Classification Search
None
See application file for complete search history.

(56) References Cited

U.S. PATENT DOCUMENTS 6,963,530 B1 * 11/2005 Thornton ................ G11B 7/127
369/121
8,097,926 B2 * 1/2012 De Graff ........... H01L 27/14618
257/419

(Continued)

FOREIGN PATENT DOCUMENTS

EP          2 312 393        4/2011   ................. G03F 7/00
WO       WO 00/63695      10/2000   ........... G01N 33/532
(Continued)

OTHER PUBLICATIONS

International Search Report for International Application No. PCT/EP2013/065442, Oct. 17, 2013.
(Continued)

*Primary Examiner* — Allan Olsen
(74) *Attorney, Agent, or Firm* — Kusner & Jaffe (57) ABSTRACT

The present invention relates to a method for producing microcarriers comprising the following steps: (a) providing a wafer having a sandwich structure comprising a bottom layer, a top layer and an insulating layer located between said bottom and top layers, (b) etching away the top layer to delineate lateral walls of bodies of the microcarriers, (c) depositing a first active layer at least on a top surface of the bodies, (d) applying a continuous polymer layer over the first active layer, (e) etching away the bottom layer and the insulating layer, (f) removing the polymer layer to release the microcarriers.

20 Claims, 7 Drawing Sheets (51) Int. Cl.
  *B81C 99/00* (2010.01)
  *G01N 33/543* (2006.01)
(52) U.S. Cl.
  CPC ............ *B01L 3/502761* (2013.01); *B01L 3/54* (2013.01); *B01L 3/545* (2013.01); *B81C 99/008* (2013.01); *G01N 33/54313* (2013.01); *B01J 2219/005* (2013.01); *B01J 2219/00502* (2013.01); *B01J 2219/00536* (2013.01); *B01J 2219/00556* (2013.01); *B01J 2219/00637* (2013.01); *B01L 2200/0647* (2013.01); *B01L 2200/10* (2013.01); *B01L 2200/12* (2013.01); *B01L 2300/0803* (2013.01); *B01L 2300/0819* (2013.01); *B01L 2300/0851* (2013.01); *B01L 2300/0893* (2013.01); *B81B 2201/058* (2013.01); *B81B 2201/06* (2013.01)

(56) References Cited

U.S. PATENT DOCUMENTS

| | | | |
|---|---|---|---|
| 8,953,314 B1 * | 2/2015 | Fedorov .................. | H01L 23/44 257/707 |
| 2001/0041369 A1 | 11/2001 | Chang et al. .................. | 436/518 |
| 2003/0140713 A1 * | 7/2003 | Ohsato .................... | G01L 5/162 73/862.041 |
| 2005/0244955 A1 | 11/2005 | Li et al. ...................... | 435/287.2 |
| 2010/0246005 A1 | 9/2010 | Moon et al. .................... | 359/569 |
| 2012/0152322 A1 * | 6/2012 | Kribus ................ | H01L 31/0687 136/249 |

FOREIGN PATENT DOCUMENTS

| | | | |
|---|---|---|---|
| WO | WO 2010/072011 | 7/2010 | ................ B01L 3/00 |
| WO | WO 2011/044708 | 4/2011 | ................ G03F 7/00 |

OTHER PUBLICATIONS

Bhardwaj et al., "Advanced silicon etching using high density plasmas," SPIE vol. 2639, 224 (1995).

Schilp et al., "Advanced Etch Tool for High Etch Rate Deep Reactive Ion Etching in Silicon Micromachining Production Environment," Proceeding MST 2001.

Madou, 2002, "Deep Reactive Ion Etching (DRIE)," Fundamentals of Microfabrication, CRC Press, pp. 105-106.

* cited by examiner

METHOD FOR PRODUCING MICROCARRIERS

FIELD OF THE INVENTION

The invention relates to a method for producing microcarriers and to a microcarrier. The invention concerns in particular microcarriers suitable for performing a biological and/or a chemical assay for research and clinical laboratories.

BACKGROUND OF THE INVENTION

Within the scope of the present invention, a microcarrier or a microparticle refers to any type of particles, respectively to any type of carriers, microscopic in size, typically with the largest dimension being from 100 nm to 300 micrometers, preferably from 1 µm to 200 µm.

According to the present invention, the term microcarrier refers to a microparticle functionalized, or adapted to be functionalized, that is containing, or adapted to contain, one or more ligands or functional units bound to the surface of the microcarrier or impregnated in its bulk. A large spectrum of chemical and biological molecules may be attached as ligands to a microcarrier. A microcarrier can have multiple functions and/or ligands. As used herein, the term functional unit is meant to define any species that modifies, attaches to, appends from, coats or is covalently or non-covalently bound to the surface of said microcarrier or impregnated in its bulk. These functions include all functions that are routinely used in high-throughput screening technology and diagnostics.

Drug discovery or screening and DNA sequencing commonly involve performing assays on very large numbers of compounds or molecules. These assays typically include, for instance, screening chemical libraries for compounds of interest or particular target molecules, or testing for chemical and biological interactions of interest between molecules. Those assays often require carrying out thousands of individual chemical and/or biological reactions.

Numerous practical problems arise from the handling of such a large number of individual reactions. The most significant problem is probably the necessity to label and track each individual reaction.

One conventional method of tracking the identity of the reactions is achieved by physically separating each reaction in a microtiter plate (microarray). The use of microtiter plates, however, carries several disadvantages like, in particular, a physical limitation to the size of microtiter plates used, and thus to the number of different reactions that may be carried out on the plates.

In light of the limitations in the use of microarrays, they are nowadays advantageously replaced by functionalized encoded microparticles to perform chemical and/or biological assays. Each functionalized encoded microparticle is provided with a code that uniquely identifies the particular ligand(s) bound to its surface. The use of such functionalized encoded microparticles allows for random processing, which means that thousands of uniquely functionalized encoded microparticles may all be mixed and subjected to an assay simultaneously. Examples of functionalized encoded microparticles are described in the international patent application WO 00/63695 and are illustrated in FIG. 1.

The international patent application WO 2010/072011 describes an assay device having at least a microfluidic channel which serves as a reaction chamber in which a plurality of functionalized encoded microparticles or microcarriers 1 (FIG. 1) can be packed. The microfluidic channel is provided with stopping means acting as filters that allow a liquid solution containing chemical and/or biological reagents to flow through while blocking the microcarriers 1 inside. The geometrical height of said microfluidic channels and the dimensions of said microcarriers 1 are chosen so that said microcarriers 1 are typically arranged in a monolayer arrangement inside each microfluidic channels preventing said microcarriers 1 to overlap each other.

Those functionalized encoded microcarriers 1 that show a favorable reaction of interest between their attached ligand(s) and the chemical and/or biological reagents flowing through may then have their code read, thereby leading to the identity of the ligand that produced the favorable reaction.

Figure 1:
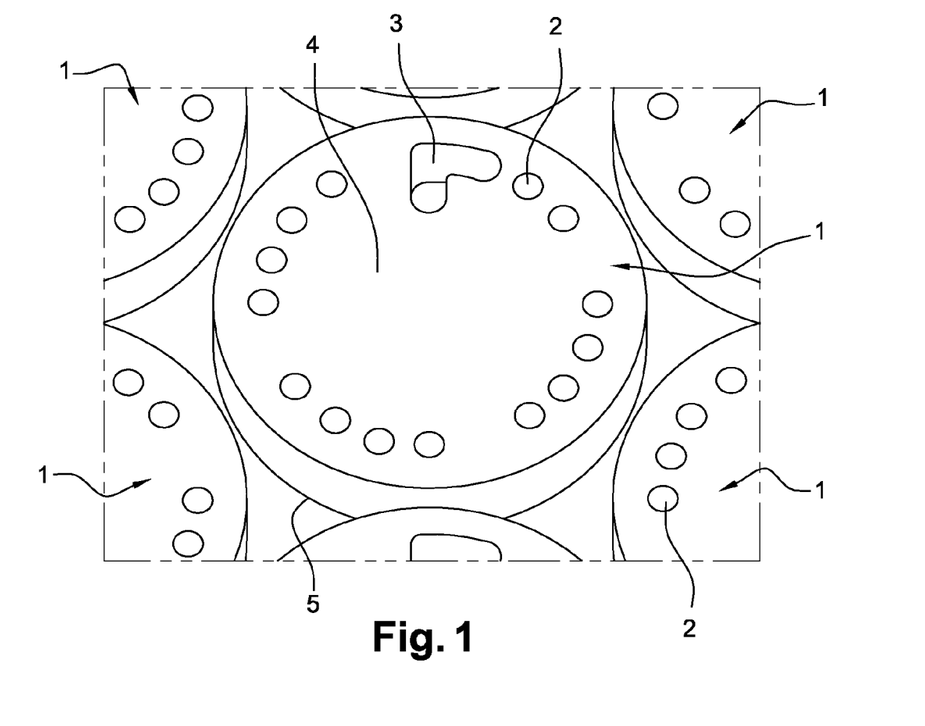
FIG. 1 illustrates a top perspective view of microcarriers according to the prior art.

The code may comprise a distinctive pattern of a plurality of traversing holes 2 and may also include an asymmetric orientation mark such as, for example, a L-shaped sign 3 (as shown in FIG. 1) or a triangle. This asymmetric orientation mark allows the distinction between the top surface 4 and the bottom surface 5 of the microcarrier 1.

The term microfluidic channel refers to a closed channel, i.e. an elongated passage for fluids, with a cross-section microscopic in size, i.e. with the smallest dimension of the cross-section being typically from about 1 to about 500 micrometers, preferably about 10 to about 200 micrometers. A microfluidic channel has a longitudinal direction, that is not necessarily a straight line, and that corresponds to the direction in which fluids are directed within the microfluidic channel, i.e. preferably essentially to the direction corresponding to the average speed vector of the fluid, assuming a laminar flow regime.

Figure 2:
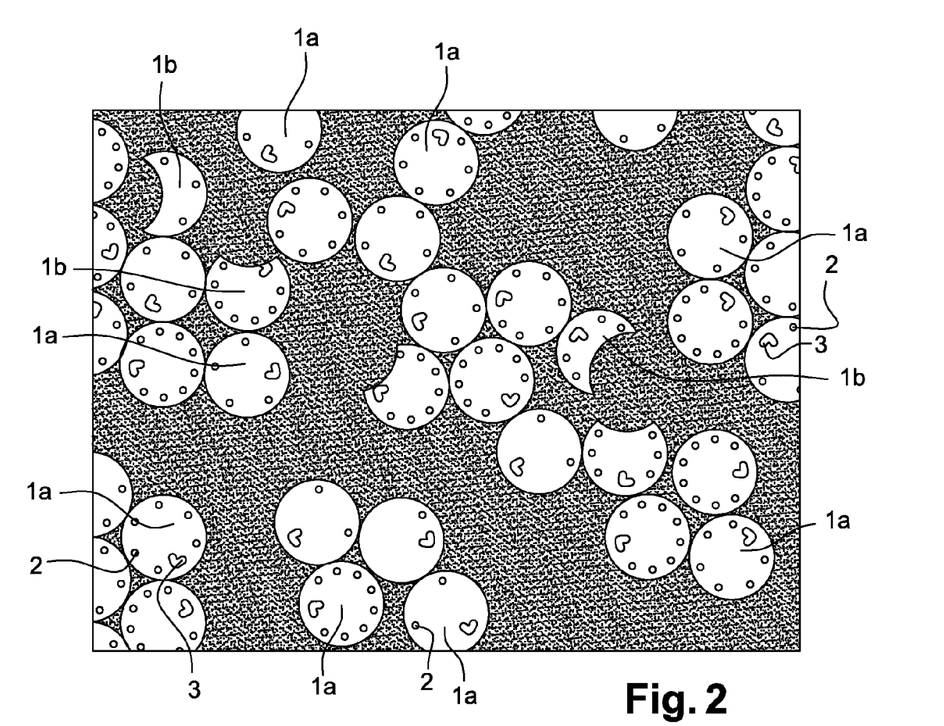
FIG. 2 illustrates fluorescent emissions on microcarriers according to the prior art, observed during an assay.

With the assay device described in WO 2010/072011, the detection of a reaction of interest can be based on continuous readout of the fluorescence intensity of each encoded microcarrier 1 present in a microfluidic channel, as depicted in FIG. 2. In other words, the presence of a target molecule in the assay will trigger a predetermined fluorescent signal. However, the predetermined fluorescent signal can be very difficult to detect due to the presence of strong fluorescent background.

It is known that coating the microcarriers with an optical layer increases the fluorescence emitted during the assay to a detectable level. For example, FIG. 2 shows a batch of coated microcarriers 1 obtained by the method described in the document WO 2011/044708, wherein an optical layer is deposited on the microcarriers 1.

However, the result of the biological assay illustrated in FIG. 2, shows different patterns of fluorescent signal emitted from the coated microcarriers 1. In particular, some microcarriers 1a emit a homogeneous and detectable fluorescent signal while other microcarriers 1b emit a partial or non-homogeneous fluorescent signal, which has most of time a shape of a crescent moon (hereafter referred to as "shadow effect"). Furthermore, some microcarriers do not emit any detectable fluorescence because they are exempt of optical layer on their surface.

Such defects render difficult the extraction of precise quantitative information during the analysis.

Figure 3:
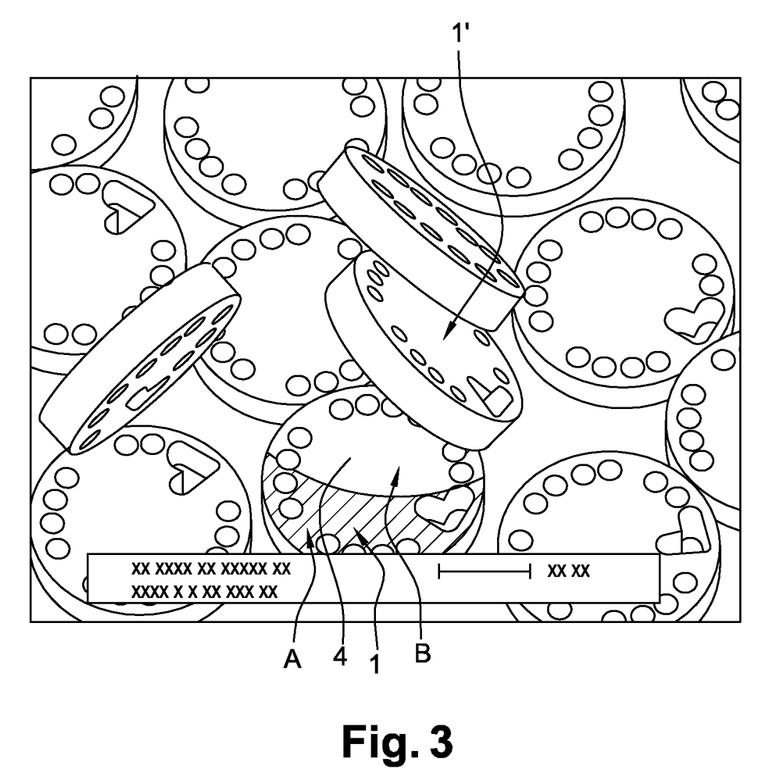
FIG. 3 illustrates a top perspective view of a batch of microcarriers before deposition of an optical layer in a manufacturing method according to the prior art.

The absence or the partial deposition of the optical layer on some microcarriers 1b results from the process involved in the document WO 2011/044708. Indeed, this process cannot avoid the partial or full overlapping between several microcarriers 1 before and during the deposition of the optical layer. Such overlapping is shown in FIG. 3 where an area A of the top surface 4 of a microcarrier 1 will be coated by an optical layer, whereas an area B of the top surface 4 of said microcarrier 1, hidden by a another microcarrier 1', will not be coated by said optical layer.

Furthermore, during the process described in WO 2011/044708, several microcarriers may flip over before coating and thus be coated on the wrong surface.

Moreover, it is impossible to separate the partly coated microcarriers 1b or the non-coated microcarriers from the well coated microcarriers 1a before performing the fluorescent assay. Indeed, the presence of an optical layer on a microcarrier is only distinguishable by a fluorescent signal emitted during the fluorescent assay.

SUMMARY OF THE INVENTION

The present invention aims to remedy all or part of the disadvantages mentioned above.

To this aim, the invention proposes a method for producing microcarriers comprising the following steps:

(a) providing a wafer having a sandwich structure comprising a bottom layer, a top layer and a insulating layer located between said bottom and top layers, (b) etching away the top layer to delineate lateral walls of bodies of the microcarriers, (c) depositing a first active layer at least on a top surface of the bodies, (d) applying a continuous polymer layer over the first active layer, (e) etching away the bottom layer and the insulating layer, (f) Removing the polymer layer to release the microcarriers.

Thus, in the method according to the invention, the deposition of the first active layer is achieved while the microcarriers are still bound to the wafer, in order to prevent the flipping or overlapping phenomena described above. The first active layer is deposited homogeneously on the entire top surface of the bodies so as to avoid the above mentioned "shadow effect" during analysis. Consequently, data integrity for precise quantitative information concerning the ligand(s) and the target molecule(s) flowing through the microchannel is preserved.

The microcarriers are also bound together until their release, thus avoiding the microcarriers to get dispersed in sensitive parts of the equipment used for their preparation, like for instance in the turbo-pumps.

Optionally, the step (c) of deposition of the first active layer is made between above mentioned steps (a) and (b). In a variant, step (a) to (f) are successively implemented.

According to an embodiment, step (e) is made by a first etching for etching selectively the bottom layer while preserving the insulating layer, for example by using an etching bath, and by a second etching for etching the insulating layer, for example by a dry etching.

If the bottom layer comprises monocristalline silicon, the etching bath may be a potassium hydroxide bath. In addition, if the insulating layer comprises silicon dioxide, the dry etching could be made by plasma etching of $CHF_3$ (fluoroform) or by plasma etching of $CF_4$.

The polymer layer may also be removed by dry etching. For example, if the polymer layer comprises parylene, it may be etched by oxygen plasma.

Additionally, a distinctive mark, for example a code, may be engraved on the microcarriers, for example between steps (b) and (c).

The same distinctive mark can be attributed to a plurality of microcarriers, for example to all microcarriers belonging to a same batch.

Thus, during an assay, different types of microcarriers can be used simultaneously and mixed together, each type having its own distinctive mark and supporting one or more specific ligand(s). In this case, the specific mark allows identifying the type of each microcarrier and its attached ligand during the assay.

When the distinctive mark is engraved before the deposition of the first active layer (step c), the thickness of said layer and the size of said distinctive mark are chosen so that the distinctive mark is readable through the first active layer.

In addition, the bottom layer and/or the top layer may comprise monocristalline silicon, the insulating layer may comprise silicon dioxide and the polymer layer may comprise parylene. According to another embodiment, the polymer layer is a glue layer which binds a support to the wafer.

Monocristalline silicon layers can be etched easily and efficiently by known etching methods such as a selective potassium hydroxide bath etching.

The insulating layer comprising silicon dioxide is able to protect the microcarriers while etching the bottom layer by using an etching bath.

The parylene layer is a highly resistant layer capable of maintaining the microcarriers before releasing.

The use of a support bound to the wafer provides enhanced mechanical properties in order to facilitate the handling of the wafer during the production of the microcarriers.

According to an embodiment of the invention, a second active layer is deposited at least on a bottom surface of the bodies of the microcarriers, for example between steps (e) and (f).

The microcarriers produced by such method comprise two opposite active layers, respectively a first active layer on the top surface of the body and a second active layer on the bottom surface of the body.

The first active layer and/or the second active layer may comprise a material having optical or magnetic properties, polycrystalline silicon and/or polytetrafluoroethylene, or a metallic layer having a high reflective index.

Using a material having optical properties will increase substantially the fluorescent signal emitted from the corresponding surface of the microcarrier. A material having magnetic properties can be used to orientate the microcarrier in a desired direction, for example. The use of polycrystalline silicon increases the porosity of the corresponding surface of the body in order to increase the effective area to be coated on said surface. Finally, polytetrafluoroethylene can be used to reduce the friction between the microcarrier and the surface on which it rests during the assay.

The first active layer and/or the second active layer may comprise an oxide or a nitride, for example silicon dioxide, or a metal layer.

Silicon dioxide may be used to smooth the corresponding surface of the body and to increase sliding of non-specific molecules on said surface. The specific signal emitted by the molecules bound to said surface is therefore enhanced while the interfering signal emitted by non-specific molecules is considerably lowered.

The invention also relates to a microcarrier obtained by a method according to the invention, comprising a body having a top surface covered with a first active layer and a bottom surface covered with a second active layer.

When both top and bottom surfaces of the bodies are covered by an active layer comprising a material having optical properties (optical layer), a reliable assay can be performed whatever the orientation of the microcarrier.

BRIEF DESCRIPTION OF THE DRAWINGS

The invention can be better understood and other details, features, and advantages of the invention appear on reading the following description made by way of non-limiting examples with reference to the accompanying drawings, in which.

DETAILED DESCRIPTION OF THE INVENTION

Figure 4:
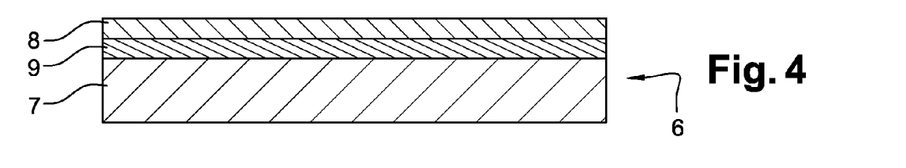
FIGS. 4 to 12 illustrate the successive steps of the method for producing microcarriers according to an embodiment of the invention.

A method for producing microcarriers according to the invention will be described with reference to FIGS. 6 to 17. This method comprises the following successive steps:

A first step, shown in FIG. 4 consists in providing a wafer 6 having a sandwich structure, which comprises a bottom layer 7, a top layer 8 and a insulating layer 9 located between said bottom and top layers 7, 8.

For example, said wafer 6 is a SOI (Silicon On Insulator) wafer having a diameter of 100 mm, a 380 µm thick bottom layer 7, a 1 µm thick insulating layer 9 and a 10 µm thick top layer 8. The top layer 8 and the bottom layer 7 are made of monocristalline silicon, and the insulating layer 9 is made of silicon dioxide.

Figures 5, 6:
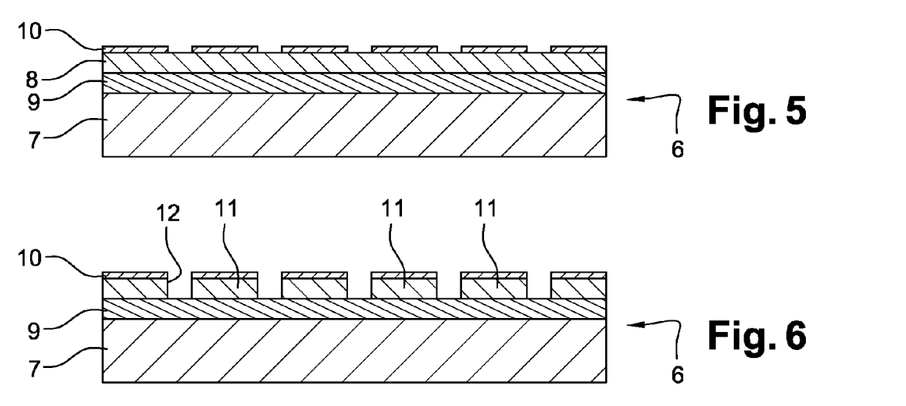

A second step, shown in FIG. 5 consists in applying a photosensitive resist layer 10 onto the top layer 8. In order to delineate the surface layout of the microcarriers, the photosensitive resist layer 10 is illuminated with UV light through a mask (not shown), such as a chrome/glass mask. Open patterns in the mask corresponding to the microcarrier layout provide a space-selective UV illumination. Photo initiators react and start polymerizing the resist layer 10 where the resist has been space-selectively illuminated. Specific chemistry is then used to remove unexposed and unreacted resist. The remaining pattern of hardened resist defines the outer shape of the microcarriers.

In a preferred embodiment herein, the remaining pattern of hardened resist further defines a code such as a binary code consisting of a series of through holes in the bodies 11 of the microcarriers, similar to the holes 2 and 3 shown in FIG. 1.

The photosensitive resist 10 may be positive or negative photoresist. One example for a positive resist is MICROPOSIT S 1805 PHOTO RESIST supplied by Shipley Company and one example for a negative photoresist is GM1040 SU-8 PHOTO EPOXY as supplied by Gersteltec Engineering Solutions. The photosensitive resist layer 10 may be applied onto the wafer 6 by different techniques known in the art, such as spray coating, or preferably spin coating.

A third step, shown in FIG. 6, consists in etching away the top layer 8 to delineate lateral walls 12 of the bodies 11 of the microcarriers. This may be done by deep reactive silicon etching (DRIE), such as the Bosch process for deep silicon etching based on DRIE (Deep Reactive Ion Etching).

The Bosch process is disclosed in the document "J. K. Bhardwaj, H. Ashraf, Proc. SPIE, 2639, 224 (1995); A. Schilp, M. Hausner, M. Puech, N. Launay, H. Karagoezoglu, F. Laermer, Advanced etch tool for high etch rate deep reactive ion etching in silicon micromachining production envi-ronment, Proceeding MST 2001, Dusseldorf". The Deep Reactive Ion Etching is disclosed in the document "Madou M J, 2002, Fundamentals of microfabrication, CRC Press".

Figure 7:
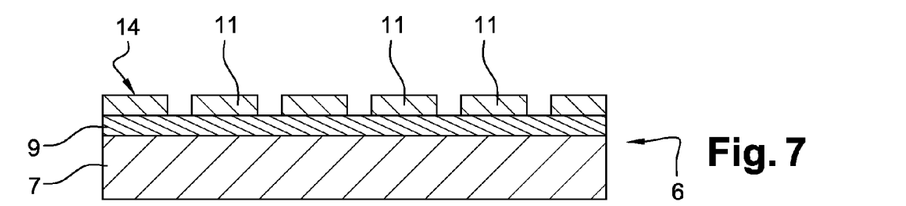

In a fourth step shown in FIG. 7, the photosensitive resist 10 is removed in a wet chemical bath. Thus, it remains a clean monocristalline silicon layer defining a series of bodies 11 that are patterned according to the design of the microcarriers.

Figure 8:
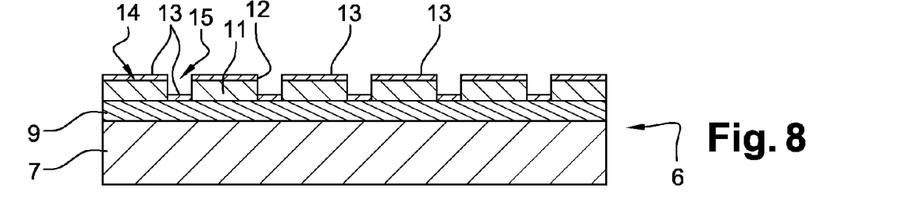

A fifth step, shown in FIG. 8, consists in depositing a first active layer 13 on the top surface 14 of the bodies 11. During the deposition, the first active layer 13 is also deposited in the bottom of the recesses 15 formed between the lateral walls 12.

The first active layer 13 is a layer having optical properties, such as an oxide layer comprising silicon dioxide. The thickness of the first layer 13 is approximately between 90 and 120 nm when working with red fluorescence labels. Any other dielectric material, such as a nitride, or a metal layer, could also be used.

Different types of oxide deposition methods can be used such as PECVD (Plasma-enhanced chemical vapor deposition), evaporation, or sputtering (Madou M J, 2002, Fundamentals of microfabrication, CRC Press). For the deposition of silicon dioxide from PECVD technique, a mixture of gases such as dichlorosilane or silane and oxygen may be used, typically at pressures from a few hundred milliTorr to a few Torr. The deposition of the silicon dioxide is performed with a temperature comprised in a range from the room temperature to 300° C.

Figure 9:
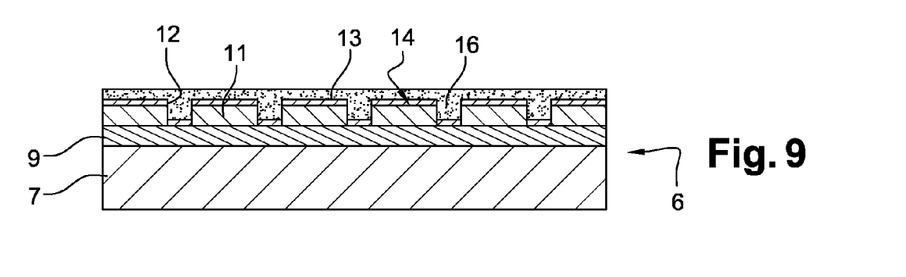

A sixth step, shown in FIG. 9, consists in applying a polymer layer 16 over the first active layer 13, for example a parylene layer or a layer made of a material known under the references ProTEK, AZ PC 520D or SX AR-PC 5000/40, respectively provided by the companies Brewer Science, Microchemical and Allresist. The thickness of said polymer layer 16 may be between 1 µm to 100 µm. This polymer layer is for example applied by Chemical Vapor Deposition (CVD) or by spin coating. A seventh step, shown in FIG. 10, consists in etching away the bottom layer 7 and the insulating layer 9.

Figure 10:
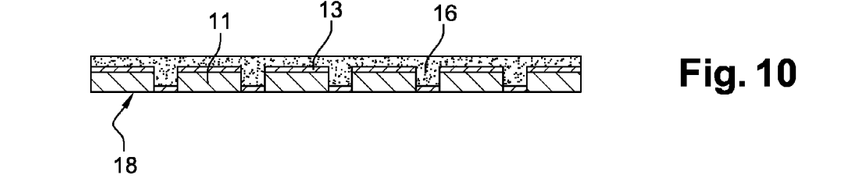

The etching away of the bottom layer 7 is performed by grinding a major portion of the bottom layer 7 and etching the rest of the bottom layer 7 by bath etching consisting in dipping the SOI wafer into a potassium hydroxide bath. Then, the insulating layer 9 is completely etched away by plasma etching of $CHF_3$ (fluoroform) or by plasma etching of $CF_4$. The etch rate of the insulating layer is controlled. In order to produce bi-layered microcarriers, the method according to the first embodiment of the invention comprises an eighth step, shown in FIG. 11, which consists in depositing a second active layer 17 onto the bottom surface 18 of the bodies 11 of the microcarriers. The second active layer 17 has also optical properties, such as an oxide layer comprising silicon dioxide. The thickness of the second layer 17 is approximately between 90 and 120 nm when working with red fluorescence labels. Any other dielectric material, such as a nitride, or a metal layer could also be used.

Figure 11:
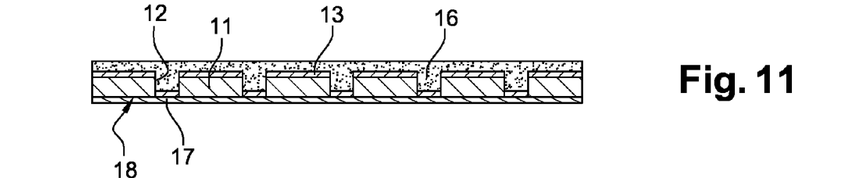

The second active layer 17 may be deposited with the same method used for the deposition of the first active layer 13.

Figure 12A:
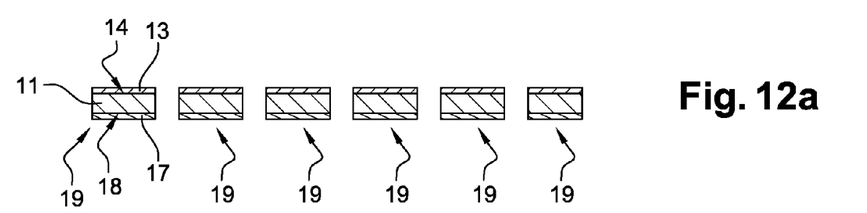

The polymer layer 16 is then etched away in order to separate and release the bi-layered microcarriers 19, as shown in FIG. 12a, for example by oxygen plasma. The etch rate is controlled. The microcarriers 19 obtained by such method each comprise a body 11 having a first active layer 13 on its top surface 14 and a second active layer 17 on its bottom surface 18. Each active layer 13, 17 covers homogeneously and continuously the corresponding surface 14, 18 of the body 11.

FIGS. 13 to 17 illustrate another embodiment of the method according to the invention.

In this embodiment, the wafer 6 shown in FIG. 8 is obtained with the same five steps.

Then, in a sixth step (FIG. 13), a support 21 is covered with a layer of glue 22. The support 21 is for example a wafer made of silicon, quartz or glass and has a thickness about 300 to 700 µm. The glue is for example a resin referenced WaferBOND HT10.10 or CR200 and provided by the company Brewer Science. The thickness of the glue layer 22 is about 10 to 100 µm, and is preferably about 50 µm.

Figure 14:
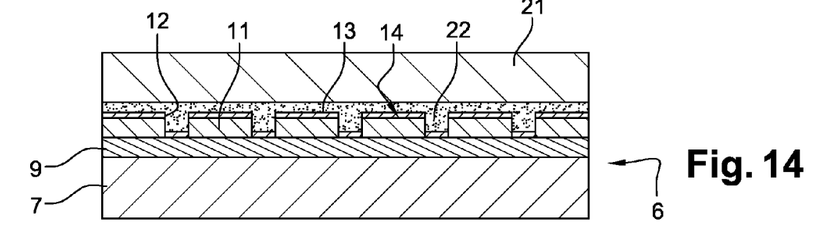

In a seventh step, shown in FIG. 14, the support 21 is bound to the wafer 6 through the glue layer 22 which contacts and adheres to the first active layer 13. Such binding is preferably made by pressing and heating the wafer 6, the support 21 and the glue layer 22.

In a variant, the glue layer 22 is directly applied on the first active layer 13 and the support 21 is applied onto the glue layer 22.

Figures 15, 16:
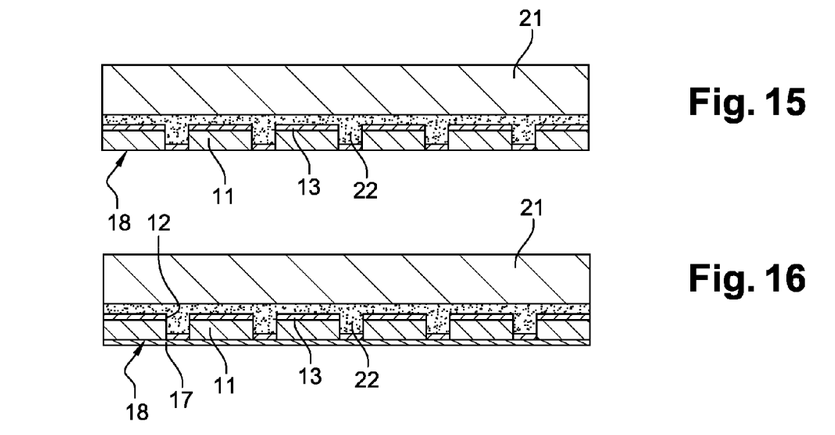

An eight step, shown in FIG. 15, consists in etching away the bottom layer 7 and the insulating layer 9. This etching step is similar to the one performed in FIG. 10.

A second active layer 17 can then be deposited onto the bottom surface 18 of the bodies 11 of the microcarriers (FIG. 16).

Figure 17:
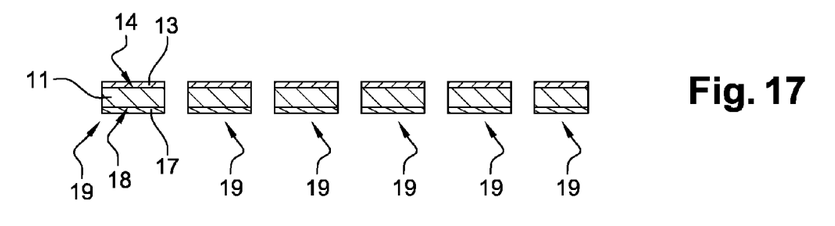
Figure 18:
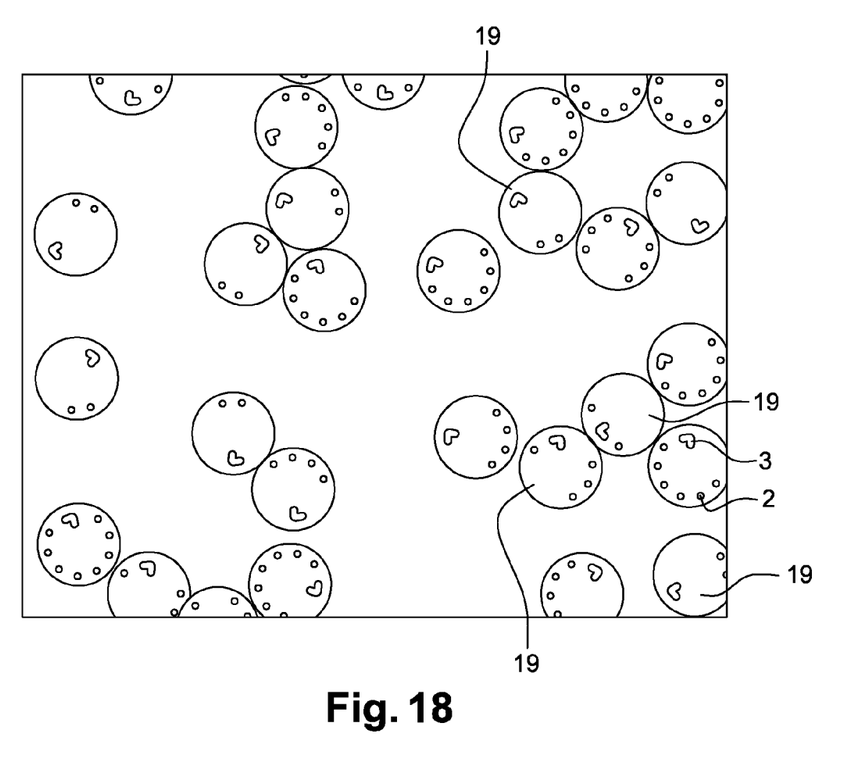
FIG. 18 illustrates fluorescent emissions on microcarriers according to the invention, observed during an assay.

Then, the support 21 is separated from the wafer 6 by removing the glue layer 22. Such removal can be made by heating the glue layer 22 or by using a solvent. The bi-layered microcarriers 19 are thus separated and released, as shown in FIG. 17.

The support 21 provides enhanced mechanical properties in order to facilitate the handling of the wafer 6 during the production of the microcarriers.

Figure 13:
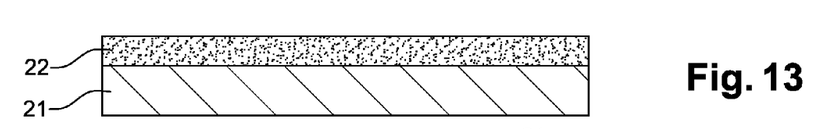
FIGS. 13 to 17 illustrate another embodiment of the invention.

As shown in FIG. 13, during an assay, the functionalized surface of each microcarrier 19 will emit a homogeneous fluorescent signal so that the above mentioned "shadow effect" is avoided. Thus, the use of such microcarriers 19 provides precise quantitative information during the assay.

The use of bi-layered microcarriers 19 is useful when it is difficult to control the orientation of the microcarriers during the analysis.

On the contrary, if the orientation of the microcarriers can be controlled, only the top surface 14 of the bodies 11 can be covered with an active layer 13.

To this aim, another embodiment of the method according to the invention proposes to etch the polymer layer 16 directly after the seventh step, shown in FIG. 10, or to remove the glue layer 22 (in order to separate the support 21 from the wafer 6) directly avec the step shown in FIG. 15.

Figure 12B:
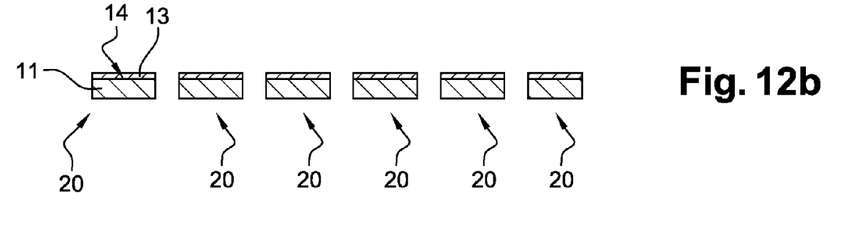

In this embodiment, as shown in FIG. 12b, microcarriers 20 having only one active layer 13 are released. This embodiment involves a less complex method, enabling the production of less expensive microcarriers 20.

In each embodiment, the released microcarriers 19, 20 may be kept in suspension in liquid containers or vessels until use in an assay. Each microcarrier 19, 20 is preferably shaped in the form of a disk and has a diameter between 1 and 200 µm, for example 40 µm.

Other embodiments of the invention will be apparent to those skilled in the art from consideration of the specification and practice of the invention disclosed herein. It is intended that the specification and example be considered as exemplary only, with the true scope and spirit of the invention being indicated by the following claims.

Having described the invention, the following is claimed:

1. A method for producing microcarriers comprising the following steps:
   (a) providing a wafer having a sandwich structure comprising a bottom layer, a top layer and an insulating layer located between said bottom and top layers,
   (b) etching away the top layer to delineate lateral walls of bodies of the microcarriers,
   (c) depositing a first layer at least on a top surface of the bodies,
   (d) applying a continuous polymer layer over the first layer,
   (e) etching away the bottom layer and the insulating layer, and
   (f) removing the polymer layer to release the microcarriers.

2. A method according to claim 1, wherein step (e) includes a first etching for etching selectively the bottom layer, and a second etching for etching selectively the insulating layer.

3. A method according to claim 2, wherein said first etching is carried out by using an etching bath.

4. A method according to claim 2, wherein said second etching is carried out by a dry etching.

5. A method according to claim 1, wherein the polymer layer is removed by dry etching.

6. A method according to claim 1, wherein said method further comprises engraving a distinctive mark on the microcarriers.

7. A method according to claim 6, wherein said distinctive mark is a code.

8. A method according to claim 6, wherein said distinctive mark is engraved between steps (b) and (c).

9. A method according to claim 1, wherein the bottom layer and/or the top layer comprise monocristalline silicon.

10. A method according to claim 1, wherein the insulating layer comprises silicon dioxide.

11. A method according to claim 1, wherein the polymer layer comprises parylene.

12. A method according to claim 1, wherein the polymer layer is a glue layer which binds a support to the wafer.

13. A method according to claim 12, wherein said support is a wafer made of silicon, quartz or glass.

14. A method according to claim 1, wherein said method further comprises depositing a second layer at least on a bottom surface of the bodies of the microcarriers.

15. A method according to claim 14, wherein said second layer is deposited between steps (e) and (f).

16. A method according to claim 14, wherein the second layer comprises a material having optical or magnetic properties, polycrystalline silicon and/or polytetrafluoroethylene, or a metal layer having a high reflective index.

17. A method according to claim 14, wherein the second layer comprises an oxide or a nitride, or a metal layer.

18. A method according to claim 1, wherein the first layer comprises a material having optical or magnetic properties, polycrystalline silicon and/or polytetrafluoroethylene, or a metal layer having a high reflective index.

19. A method according to claim 1, wherein the first layer comprises an oxide or a nitride, or a metal layer.

20. A method according to claim 19, wherein said oxide is silicon dioxide.

* * * * *